US 8,979,752 B2

(12) United States Patent
Matsumura

(10) Patent No.: US 8,979,752 B2
(45) Date of Patent: Mar. 17, 2015

(54) RIB SPREADER

(75) Inventor: Kenichi Matsumura, Tokyo (JP)

(73) Assignee: Medical Pine Co., Ltd., Tokyo (JP)

( * ) Notice: Subject to any disclaimer, the term of this patent is extended or adjusted under 35 U.S.C. 154(b) by 217 days.

(21) Appl. No.: 13/578,440

(22) PCT Filed: Feb. 10, 2011

(86) PCT No.: PCT/JP2011/052852
§ 371 (c)(1),
(2), (4) Date: Aug. 10, 2012

(87) PCT Pub. No.: WO2011/099553
PCT Pub. Date: Aug. 18, 2011

(65) Prior Publication Data
US 2012/0316401 A1    Dec. 13, 2012

(30) Foreign Application Priority Data

Feb. 12, 2010    (JP) ................... 2010-029020
Jul. 6, 2010     (JP) ................... 2010-154150
Oct. 22, 2010    (JP) ................... 2010-237644

(51) Int. Cl.
*A61B 1/32*    (2006.01)
*A61B 17/02*   (2006.01)

(52) U.S. Cl.
CPC .................. *A61B 17/0206* (2013.01)
USPC ............ 600/235; 600/210; 600/215; 600/232

(58) Field of Classification Search
USPC ......... 600/210, 214, 215, 217, 219, 224, 227, 600/231, 232, 233, 235; 606/90
See application file for complete search history.

(56) References Cited

U.S. PATENT DOCUMENTS

| 2,670,731 A | 3/1954 | Zoll et al |
| 5,616,117 A | 4/1997 | Dinkler et al. |
| 5,772,583 A | 6/1998 | Wright et al. |

(Continued)

FOREIGN PATENT DOCUMENTS

| DE | 198 17 337 B4 | 10/1999 |
| JP | 9-529 A | 1/1997 |

(Continued)

OTHER PUBLICATIONS

International Search Report dated May 20, 2011 issued in International Appln. No. PCT/JP2011/052852.
Japanese Office Action dated Oct. 28, 2014 issed in counterpart Japanese Application No. 2011-553884.

*Primary Examiner* — Michael T Schaper
*Assistant Examiner* — Tracy Kamikawa
(74) *Attorney, Agent, or Firm* — Holtz, Holtz, Goodman & Chick PC

(57) ABSTRACT

Disclosed is a rib spreader including a stationary arm having a first bent portion; a first hook having a contact surface to contact with one incision plane of a sternum of human, and attached to the stationary arm ahead of the first bent portion so as to be pivotable over a predetermined angular range; a rack fixed to the base end of the stationary arm at a predetermined angle and curved archwise; a movable arm supported at the base end of the movable arm by the rack so as to be movable along the rack, to thereby vary the distance from the stationary arm; and a second hook having a contact surface to contact with the other incision plane, and is attached to the movable arm ahead of the second bent portion so as to be pivotable over a predetermined angular range.

8 Claims, 18 Drawing Sheets

(56) References Cited

U.S. PATENT DOCUMENTS

| | | |
|---|---|---|
| 6,206,828 B1 * | 3/2001 | Wright .................. 600/232 |
| 6,500,116 B1 * | 12/2002 | Knapp .................. 600/232 |
| 7,654,954 B1 * | 2/2010 | Phillips et al. ............ 600/228 |
| 2001/0041828 A1 | 11/2001 | Deckman et al. |
| 2004/0127773 A1 | 7/2004 | Douglas |
| 2007/0038032 A1 | 2/2007 | DeCanniere et al. |
| 2007/0156027 A1 * | 7/2007 | Hu et al. .................. 600/232 |

FOREIGN PATENT DOCUMENTS

| | | |
|---|---|---|
| JP | 3077381 U | 2/2001 |
| JP | 2004-255173 A | 9/2004 |
| JP | 2009-504214 A | 2/2009 |
| JP | 2009-261811 A | 11/2009 |

\* cited by examiner

RIB SPREADER

This application is a U.S. National Phase Application under 35 USC 371 of International Application PCT/JP2011/052852 filed Feb. 10, 2011.

FIELD OF THE INVENTION

The present invention relates to a rib spreader used in median sternotomy, and more specifically to a rib spreader capable of preventing fracture of sternum or crush of sternum stump which may otherwise occur during median sternotomy.

DESCRIPTION OF RELATED ART

Median sternotomy, by which sternum is vertically incised at the center thereof, is adopted in most medical cases in need of cardiac or macrovascular surgeries. Portions of the sternum centrally incised and split into the left and right are laterally displaced by a rib spreader, for the convenience of surgery proceeded in the thus-opened space.

The median sternotomy has, however, been anticipated for a risk of sternum fracture, particularly high in children, in the process of displacement by the rib spreader. Patent Document 1 proposes a rib spreader capable of preventing the sternum fracture. More specifically, proposed are an assistive tool for rib spreader and a rib spreader attached therewith, which are capable of stopping bleeding at the sternum stump when the portions of sternum split by the median sternotomy are displaced, and of also preventing the sternum fracture and crush of the sternum stump. Patent Document 2 proposes a sternum elevator capable of, during elevation of sternum, keeping a state of surface contact of the tool conforming to the geometry of sternum, free from a risk of damaging the sternum, and is therefore stress-free from the viewpoint of labor saving in initial opening of the sternum.

The thorax of human body is composed of three parts: vertebral column (thoracic vertebra), rib, and sternum, which give an "O-shaped" cross section. The cross section changes into "C-shape" when the sternum is displaced by a rib spreader after median sternotomy. The vertebral column (thoracic vertebra) and the rib deform as a whole under force applied to the sternum. More specifically, when the sternum after median sternotomy is applied with force using the conventional rib spreader described in Patent Document 1 or 2, having a straight rack, in the direction of opening of the sternum, typically under a linear force applied oppositely to the left and right, unnatural deformation or concentration of pressure will not occur so long as the distance of spreading of the incised sternum is small. However, as the distance of spreading of sternum increases, the sternum will deform unnaturally as illustrated in FIG. 9, due to generation of component of force in the direction which acts to bring the sternum apart from the vertebral column (thoracic vertebra), even enough to detach the rib spreader during the displacement in some cases. Since the portions of sternum in this case rotates to open a hinge made of the vertebral column (thoracic vertebra) and the ribs, the left and right incision planes of the sternum are no longer in parallel with each other. Since the distance of spreading of the incision planes measured on the side more closer to the human body will be shorter than the distance of spreading measured on the side more distant from the human body, the pressure is concentrated to the closer side. Such unnatural deformation and concentration of pressure may cause fracture of sternum or crush of sternum stump as a consequence, and the patient may feel unpleasant after surgery due to an excessive spreading of the ribs. In contrast, Patent Document 3 proposes a rib spreader which has a rack curved archwise along a cylindrical surface.

PRIOR ART DOCUMENTS

Patent Document

[Patent Document 1] Japanese Laid-Open Patent Publication No. 2009-261811
[Patent Document 2] Japanese Laid-Open Patent Publication No. 2004-255173
[Patent Document 3] U.S. Pat. No. 5,772,583

SUMMARY

Problems to be Solved by the Invention

The conventional rib spreaders and the sternum elevator did not, however, have a function of ensuring a good field of view and a sufficient working area for surgery, by sliding a hook so as to adjust the position thereof. In addition, according to the configuration in which a stationary arm having a bent portion and a movable arm having a bent portion are coupled via the rack which curves archwise along the cylindrical surface, the distance of spreading of sternum measured on the side closer to the superior thoracic aperture becomes shorter than the distance of spreading of sternum measured on the side closer to the inferior thoracic aperture as the distance of spreading of sternum increases. This makes the upper portion of heart less readily recognizable as a consequence. The conventional tools are therefore less satisfactory, in terms of ensuring a good field of view and a sufficient working area for surgery, and of ensuring a good operability.

Considering the conventional problems as described in the above, it is therefore a first object of the present invention to provide a rib spreader capable of preventing fracture of sternum or crush of sternum stump in the displacement of sternum after median sternotomy, by displacing the sternum naturally by an uniform force without causing unnatural deformation or concentration of pressure. It is therefore a second object of the present invention to provide a rib spreader capable of absorbing personal differences in the length of sternum of patients or state of deformation of sternum during displacement, and capable of ensuring a good field of view and a sufficient working area for surgery, and of ensuring a good operability and flexibility of adoption.

Means for Solving the Problems

According to one aspect of the present invention, there is provided a rib spreader which includes: a stationary arm having at least a first bent portion; at least one first hook which has a contact surface to be brought into contact with one of two incision planes of a sternum of human body, and is attached to the stationary arm ahead of the first bent portion so as to be pivotable over a predetermined angular range; a rack which is fixed to the base end of the stationary arm at a predetermined angle, and is curved archwise; a movable arm which has at least a second bent portion, and is supported at the base end thereof by the rack so as to be movable along the rack, to thereby vary the distance from the stationary arm; and at least one second hook which has a contact surface to be brought into contact with the other one of the two incision planes, and is attached to the movable arm ahead of the second bent portion so as to be pivotable over a predetermined angular range.

The rack preferably has a rectangular cross section normal to the longitudinal direction of the rack; has two side faces corresponding to two long edges of the rectangle, and are curved archwise along two concentrically-arranged cylindrical surfaces; has two side faces which are two surfaces corresponding to two short edges of the rectangle, and are arranged concentrically around the same center axis but respectively normal to the two cylindrical surfaces; and is toothed on one of the two surfaces, so as to allow the movable arm to move along the rack.

A radius of curvature of the rack is determined based on the distance of the contact surface of the first hook and the contact surface of the second hook and the angle of inclination of the individual contact surfaces, the distance and the angle being observed when the rib spreader is attached to laterally displace the sternum of human body.

It is preferable that the stationary arm and the movable arm respectively have a third bent portion and a fourth bent portion which bend in the direction opposite to the first bent portion and the second bent portion, respectively at portions between the base ends thereof where the rack is fixed, and the first bent portion and the second bent portion, and the angle of the third bent portion and the angle of the fourth bent portion are preferably set so that the distance between the base end-side apex of the contact surface of the first hook and the base end-side apex of the contact surface of the second hook is made nearly equal to the distance between the front end-side apex of the contact surface of the first hook and the front end-side apex of the contact surface of the second hook.

The rack preferably has a rectangular cross section normal to the longitudinal direction of the rack; has two side faces corresponding to two long edges of the rectangle, and are curved archwise along two first conical surfaces which have predetermined conical angles assumed around the same center axis; has two side faces corresponding to two short edges of the rectangle, and are curved archwise along two second conical surfaces which are arranged concentrically around the same center axis but respectively aligned normal to the two first conical surfaces; and is toothed on one of the two side faces which are respectively curved along the two second conical surfaces, so as to allow the movable arm to move along the rack.

The radius of curvature of the rack, measured at a predetermined position thereof away from the center axis of the first conical surface, is preferably determined based on the distance between the contact surface of the first hook and the contact surface of the second hook and the individual angles of inclination of the contact surfaces, the distance and the angle being observed when the rib spreader is attached to laterally displace the sternum of human body.

The conical angle of the first conical surface is preferably set so that the distance between the base end-side apex of the contact surface of the first hook and the base end-side apex of the contact surface of the second hook, is made nearly equal to the distance between the front end-side apex of the contact surface of the first hook and the front end-side apex of the contact surface of the second hook.

It is preferable that the first bent portion has a first intermediate bent portion and a first front end bent portion, the first hook has a first intermediate hook and a first front end hook, the first intermediate hook is engaged with a first oblong hole, which is provided between the first intermediate bent portion and the first front end bent portion of the stationary arm, and is oblong in the longitudinal direction of the stationary arm, so as to be slidable therein and pivotable over a predetermined angular range, the second bent portion has a second intermediate bent portion and a second front end bent portion, the second hook has a second intermediate hook, and a second front end hook, and the second intermediate hook is engaged with a second oblong hole, which is provided between the second intermediate bent portion and the second front end bent portion of the movable arm, so as to be slidable therein and pivotable over a predetermined angular range.

It is preferable that the stationary arm further has a first front end hole which is provided ahead of the first front end bent portion, the first front end hook engages with the first front end hole so as to be pivotable over a predetermined angular range, the movable arm further has a second front end hole which is provided ahead of the second front end bent portion, and the second front end hook engages with the second front end hole so as to be pivotable over a predetermined angular range.

It is preferable that the bend angle of the first and second intermediate bent portion, and the bend angle of the first and second front end bent portion are respectively set based on curved geometry of the sternum of human body.

The maximum distance between the contact surface of the first intermediate hook and the contact surface of the first front end hook, and the maximum distance between the contact surface of the second intermediate hook and the contact surface of the second front end hook, are preferably set based on the length of the sternum of human body.

The maximum angular range over which the individual contact surfaces of the first intermediate hook and the first front end hook are pivotable about the stationary arm, and, maximum angular range over which the individual contact surfaces of the second intermediate hook and the second front end hook are pivotable about the movable arm, are preferably ±25° or larger and ±35° or smaller.

The individual fixing nuts with which the first intermediate hook and the first front end hook are respectively engaged to the first oblong hole and the first front end hole of the stationary arm, are preferably embedded into the stationary arm, so as to align the top surfaces of the individual fixing nuts to a level not exceeding that of the top surface of the stationary arm, and the individual fixing nuts with which the second intermediate hook and the second front end hook are respectively engaged to the second oblong hole and the second front end hole of the movable arm, are preferably embedded into the movable arm, so as to align the top surfaces of the individual fixing nuts to a level not exceeding that of the top surface of the movable arm.

The stationary arm and the movable arm are preferably plated in mat black.

Effect of the Invention

According to the present invention, by virtue of the rack which is bent archwise, the sternum may be prevented from unnaturally deformed during displacement. Additionally according to the present invention, the incision planes of sternum and the contact surfaces of the individual hooks may be kept in surface contact conforming to changes in the angle of incision planes of sternum, thereby difference in stress between the portions distant from the human body and closer to the human body may be reduced. As a consequence, fracture of sternum or crush of sternum stump are avoidable.

The individual embodiments of the present invention give effects as follows. By configuring the individual hook so as to be independently pivotable about the individual arms, the difference in stress between the portions of the individual contact surfaces on the superior thoracic aperture side and the inferior thoracic aperture side may be reduced. By configuring the intermediate hooks of the individual arms so as to be slidable, position of the hooks are adjustable in situ depending on the length of sternum of the patient, and a state of deformation of sternum during displacement. By configuring the stationary arm and the movable arm without forming on the surfaces thereof any projection such as nut, accidental hooking of surgical suture is avoidable. By using the rack curved archwise along a conical surface having a predetermined conical angle, or by using the rack curved archwise along the cylindrical surface together with the arm having a base end bent portion, the upper portion of heart may be more readily recognizable. As a consequence, personal differences such as the length of sternum of the patient, or the state of deformation of sternum during displacement may be absorbed, and thereby a good field of view and a sufficient working area for surgery, and a good operability and flexibility of adoption may be ensured.

Moreover, by configuring each of the stationary arm and the movable arm to have the intermediate bent portion and the front end bent portion, different changes in the angle of sternum between the portions thereof on the superior thoracic aperture side and the inferior thoracic aperture side may be absorbed, thereby both of the contact surfaces of the front end hooks brought into contact with the superior thoracic aperture side, and the contact surfaces of the intermediate hooks brought into contact with the inferior thoracic aperture side, may keep the state of surface contact with the incision planes of sternum. In other words, the unnatural deformation which may otherwise be anticipated in the process of displacement by which the sternum is displaced concomitantly on the superior thoracic aperture side and the inferior thoracic aperture side thereof, is avoidable. At the same time, difference in stress exerted on the contact surfaces between the portions distant from the human body and closer to the human body may be reduced. Accordingly, similarly as described in the above, fracture of sternum and crush of sternum stump are avoidable.

DESCRIPTION OF THE PREFERRED EMBODIMENTS

The rib spreader of the present invention will be detailed referring to the preferred embodiments illustrated in the attached drawings.

Figure 1:
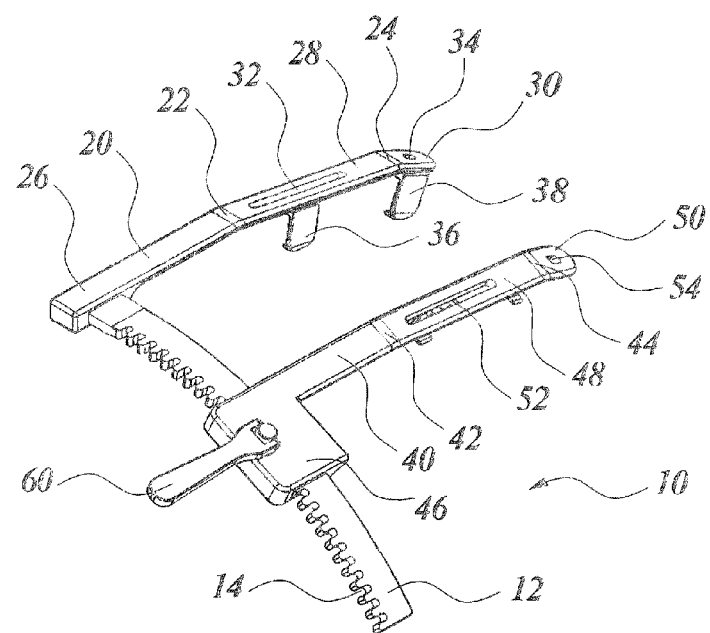
FIG. 1 is a perspective view illustrating a rib spreader according to a first embodiment of the present invention.
Figure 2:
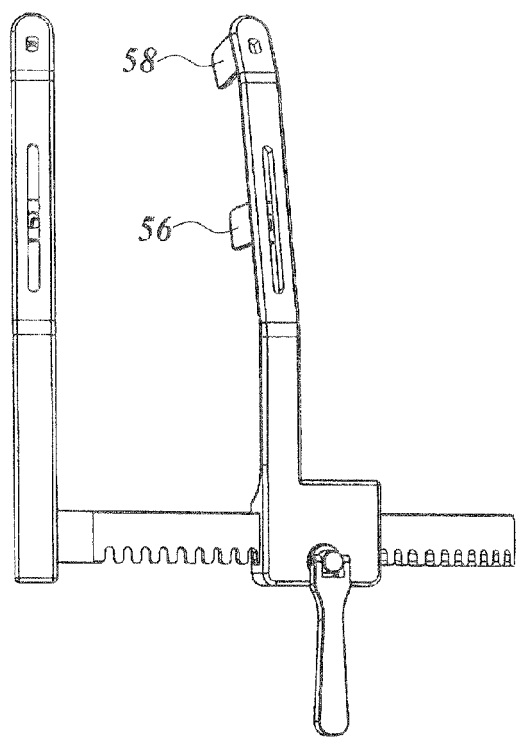
FIG. 2 is a plan view illustrating the rib spreader illustrated in FIG. 1.
Figure 3:
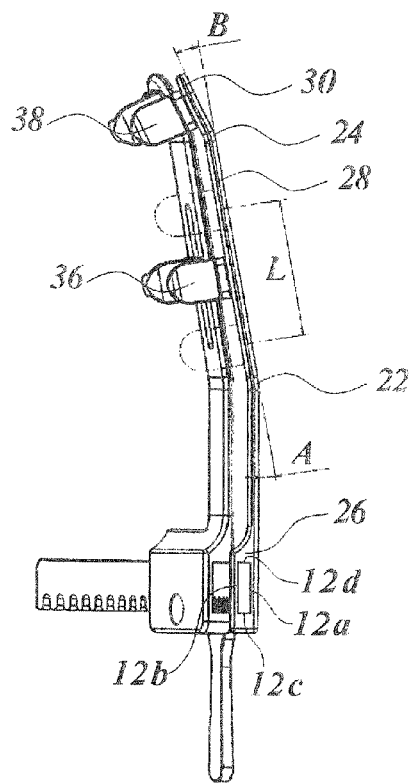
FIG. 3 is a left side elevation of the rib spreader illustrated in FIG. 1.
Figure 4:
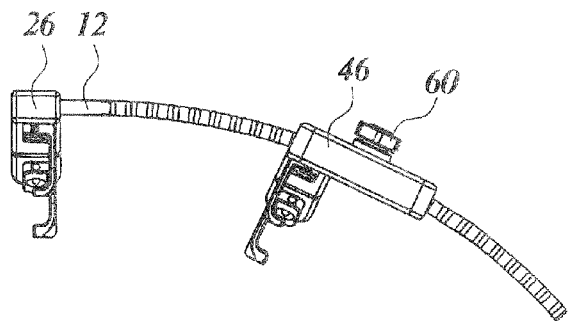
FIG. 4 is a front elevation of the rib spreader illustrated in FIG. 1.

FIG. 1 is a perspective view illustrating a rib spreader according to a first embodiment of the present invention, FIG. 2 is a plan view of the rib spreader illustrated in FIG. 1, FIG. 3 is a left side elevation of the rib spreader illustrated in FIG. 1, and FIG. 4 is a front elevation of the rib spreader illustrated in FIG. 1. Note that, in FIGS. 1 to 4, nuts for fixing the individual hooks are not illustrated.

A rib spreader 10 is configured by a stationary arm 20, a movable arm 40, and a rack 12 which relatively varies the distance between the both. The rack 12 is a thin, long plate-like component which curves archwise along a cylindrical surface. The rack 12 has teeth 14 on the side face corresponding to one short edge of the rectangular cross section taken normal to the longitudinal direction thereof. The rack 12 performs similarly to a rack in a rack-and-pinion gear mechanism. The rack 12 is fixed, on one longitudinal end face thereof, to the stationary arm 20 at a base end 26 thereof, so as to align the longitudinal direction of the stationary arm 20 nearly normal to the longitudinal direction of the rack 12. The stationary arm 20 is configured by the base end 26 fixed to the rack 12, a flat intermediate portion 28, and a flat front end portion 30. The stationary arm 20 has an intermediate bent portion 22 between the base end 26 and the intermediate portion 28, and has a front end bent portion 24 between the intermediate portion 28 and the front end portion 30. The intermediate portion 28 has an oblong hole 32. The front end portion 30 has a hole 34. An intermediate hook 36 is engaged with the oblong hole 32 so as to be slidable and pivotable therein. An front end hook 38 is engaged with the hole 34 so as to be pivotable independently from the intermediate hook 36.

The movable arm 40 is supported, at a base end 46 thereof, by a rack 12, so as to align the longitudinal direction of the movable arm 40 nearly in parallel with the longitudinal direction of the stationary arm 20. The distance from the stationary arm 20 to the movable arm 40 is adjustable by rotating a handle 60. The movable arm 40 is configured by the base end 46 fixed to the rack 12, a flat intermediate portion 48, and a flat front end portion 50. The movable arm 40 has an intermediate bent portion 42 between the base end 46 and the intermediate portion 48, and has a front end bent portion 44 between the intermediate portion 48 and the front end portion 50. The intermediate portion 48 has an oblong hole 52. The front end portion 50 has a hole 54. An intermediate hook 56 is engaged with the oblong hole 52 so as to be pivotable and slidable therein. An front end hook 58 is engaged with the hole 54 so as to be pivotable independently from the intermediate hook 56.

Surgical light reflected or scattered on the stationary arm 20 and the movable arm 40 may degrade the field of view of a surgeon. In addition, any diseased part reflected on the tool may induce misoperation by the surgeon. In order to avoid such nonconformities, the stationary arm 20, the movable arm 40, the intermediate hooks 36, 56, and the front end hooks 38, 58 are plated in mat black.

In the present invention, a publicly-known mechanism is adopted to transmit rotational motion of the handle 60 to the teeth 14 which are provided to the side face on the short edge side of the rectangular cross section taken normal to the longitudinal direction of the rack 12, so as to translate the movable arm 40. For example, Japanese Laid-Open Patent Publication No. H09-299373 describes a method of using two shafts. More specifically, the base end 46 of the movable arm 40 has incorporated therein two shafts placed equally away from the axis of rotation of the handle 60, at 180° intervals, and in parallel to the axis of rotation. The two shafts rotate together with the handle 60 around the axis of rotation thereof, while being engaged with the teeth 14, to thereby translate the movable arm 40 in a manner similar to the rack-and-pinion gear mechanism.

Figure 5:
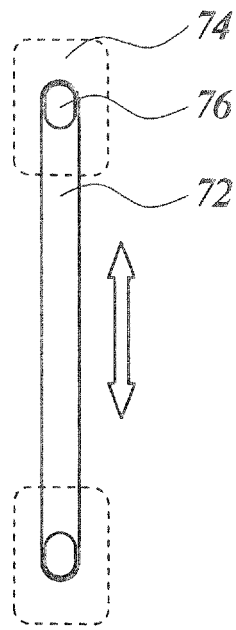
FIG. 5 is a cross sectional view schematically illustrating motion of an intermediate hook of the rib spreader illustrated in FIG. 1.

FIG. 5 is a cross sectional view schematically illustrating motion of the intermediate hook of the rib spreader illustrated in FIG. 1. An oblong hole 72 corresponds both to the oblong hole 32 of the stationary arm 20 and the oblong hole 52 of the movable arm 40. A hook 74 corresponds both to the intermediate hook 36 of the stationary arm 20 and the intermediate hook 56 of the movable arm 40. The hook 74 has a hook stem 76 fixed thereto. The hook stem 76 has, in portions of the side face thereof, two nearly-parallel flat surfaces formed by milling. The hook stem 76 is slidable in the oblong hole 72 having a width larger than the distance between these two surfaces.

Figure 6:
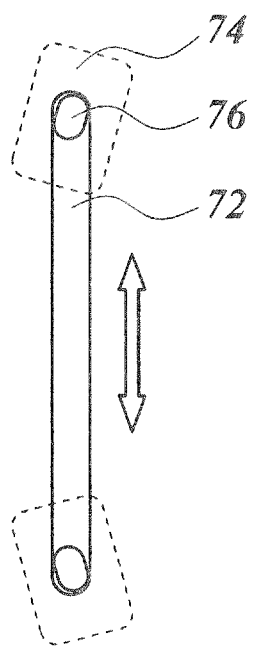
FIG. 6 is a cross sectional view supplementarily explaining motion of the intermediate hook illustrated in FIG. 5.

FIG. 6 is a cross sectional view illustrating an exemplary state of pivoting of the hook 74. The pivoting of the hook 74 is restricted to a predetermined angle, by adjusting the width of the oblong hole 72 smaller than the maximum diameter of the hook stem 76. This contributes to prevent a contact surface 82 (see FIG. 7) of the hook 74 brought into contact with each incision plane of sternum, or a U-shaped inner surface of the hook 74, from being faced to an inappropriate direction during use. Any surface other than the contact surface 82 brought into contact with the incision plane of sternum may result in fracture of sternum and so forth. On the other hand, it may considerably degrade the operability to check the direction of the contact surfaces 82 of the four hooks 72 engaged with the rib spreader 10, and correct the direction depending on needs, for the purpose of avoiding the nonconformities described in the above. Note that, in order to slide the hook 74 in parallel with the contact surface 82, the two flat surfaces, formed by milling on portions of the side face of the hook stem 76, have to be in parallel with the contact surface 82.

Figure 7:
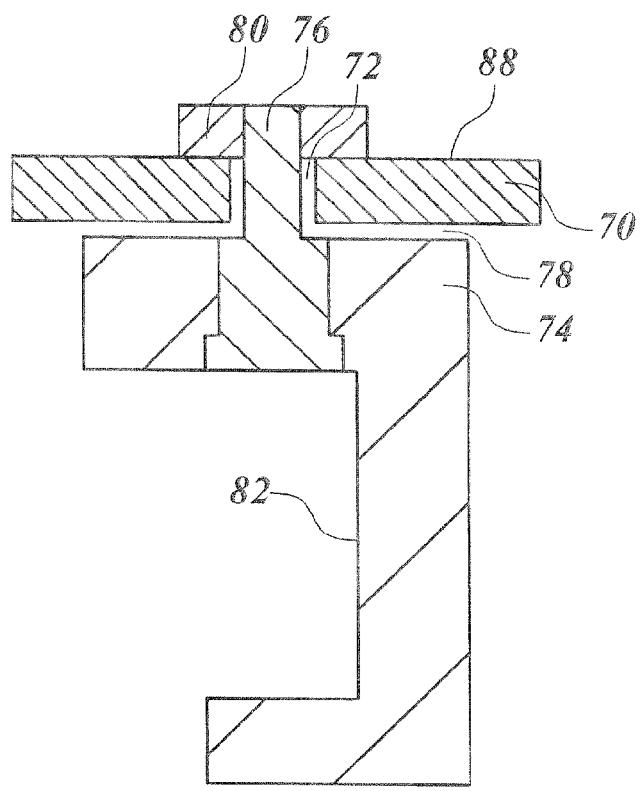
FIG. 7 is a cross sectional view illustrating a fixed structure of the intermediate hook illustrated in FIG. 5.

FIG. 7 is a cross sectional view of a fixed structure of the intermediate hook illustrated in FIG. 5, taken along a line drawn laterally through the center of the hook stem 76 in FIG. 5. The hook stem 76 fixed to the hook 74 is inserted in the oblong hole 72 of an arm 70 which corresponds to the stationary arm 20 and the movable arm 40. A nut 80 is fitted to the axial end of the hook stem 76 projected out from the top surface 88 of the arm 70. There is a gap 78 provided between the arm 70 and the hook 74. The gap 78 allows the hook 74 to slide and to pivot. There is also the gap, as described in the above, between the flat portion of the side faces of the oblong hole 72 and the flat portions of the hook stem 76 which allows the hook 74 to slide and to pivot. While FIG. 7 illustrates the contact surface 82 faced to the left, the contact surface 82 will be faced to the reverse direction depending on whether the arm 70 represents the stationary arm 20 or the movable arm 40.

It is not necessary for the front end hook 38 of the stationary arm 20 and the front end hook 58 of the movable arm 40 to be slidable. They may even degrade the usability if they are made slidable, since a larger number of portions have to be adjusted. Accordingly, the hook stem 76 fixed to the hook 74 is inserted respectively in the hole 34 of the stationary arm 20 and in the hole 54 of the movable arm 40, which are provided so as to allow therein pivoting only. A nut 80 is fitted to the axial end of the hook stem 76 projected out from the top surface 88 of the arm 70. Each of the hole 34 and the hole 54 is functionally an oblong hole which allows therein no slidable distance for the hook 74. More strictly, each of the hole 34 and the hole 54 is a hole with a geometry derived from a circle with the exception of two segments divided by two nearly-parallel chords. The gap 78 is provided between the arm 70 and the hook 74. The gap 78 allows the hook 74 to pivot therein. A gap is provided between each of the flat portions of the side faces of the hole 34 and the hole 54, and the flat portions of the hook stem 76. The gap allows the hook 74 to pivot therein. The pivoting of the hook 74 is restricted to a predetermined angle, by adjusting the distance between the flat portions of the side faces of the hole 34 and the hole 54 smaller than the maximum diameter of the hook stem 76.

Figure 8:
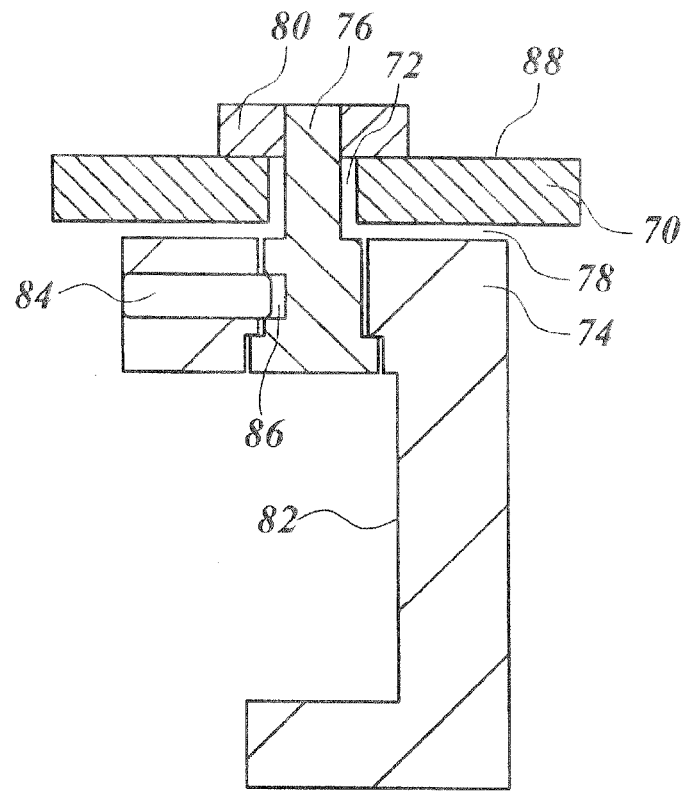
FIG. 8 is a cross sectional view illustrating another fixed structure of the intermediate hook illustrated in FIG. 5.

While embodiments illustrated in FIGS. 5 to 7 have the hook stem 76 fixed to the hook 74, another possible configuration may have the hook 74 and the hook stem 76 relatively pivotable to a predetermined angle. This embodiment is typically illustrated in FIG. 8. In FIG. 8, a hole is newly formed in the hook 74 while being aligned to the center of the hole for accommodating the hook stem 76. The new hole is nearly normally to the hole for accommodating the hook stem 76. A pin 84 is inserted into the new hole so as to fit it to a flat portion, formed by milling, of the side face of the hook stem 76. The maximum angular range of pivoting is adjustable, depending on the size of the gap 86 between the flat portion and the end face of the pin 84. In the front end hooks 38, 58 adopted by this method of fixing, the hook 74 and the hook stem 76 are relatively pivotable to a predetermined angle, so that the hook stem 76 may completely be fitted respectively to the hole 34 and the hole 54. In other words, the hook stem 76 may be pressed into, and thereby fixed to, the hole 34 and the hole 54 without using the nut 80.

When the rib spreader of the present invention is used, first, while keeping the stationary arm 20 and the movable arm 40 in close and keeping the intermediate hooks 36, 56 of the individual arms slid towards the front end hooks 38, 58, the front end hooks 38, 58 of the individual arms are brought into contact with the superior thoracic aperture side of the incision planes of the patient's sternum. Next, the intermediate hooks 36, 56 of the individual arms are brought into contact with the inferior thoracic aperture side of the sternum. Then, the handle 60 is rotated so as to gradually expand the distance between the contact surfaces 82 of the two hooks 36, 38 on the stationary arm 20 and the contact surfaces 82 of the two hooks 56, 58 on the movable arm 40 to thereby laterally displace the sternum. During the displacement, the intermediate hooks 36, 56 of the individual arms are appropriately slid apart from the front end hooks 38, 58 and adjusted in place, to thereby ensure a good field of view and a sufficient working area for surgery. Since the deformation of ribs is predominant among those of three members composing the thorax: which are vertebral column (thoracic vertebra), ribs, and sternum, so that it is not possible to set the radius of curvature of the rack based on the radius of curvature of human thorax, or based on the distance between the sternum and the vertebral column (thoracic vertebra). Accordingly, it is usual to design the radius of curvature of the rack using an empirically obtained dimension, which is often smaller than the radius of curvature of the human thorax, or than the distance between the sternum and the vertebral column (thoracic vertebra).

It is therefore appropriate to set the radius of curvature of the rack, which curves archwise along a cylindrical surface, based on the distance between the contact surfaces brought apart on the left and right after the displacement of the human sternum, and based on the angle of inclination of the contact surfaces. This will be detailed later in relation to the explanation of FIG. 14.

It is, therefore, appropriate to set the maximum distance between the contact surfaces 82 of the intermediate hooks 36, 56 and the contact surfaces 82 of the front end hooks 38, 58, when the intermediate hooks 36, 56 of the arms are slid apart from the front end hooks 38, 58 (that is, towards the rack 12), based on the length of human sternum. The total dimensional range which is necessary to cover from infants to adults is shared by a predetermined number of product lines each of which being assigned to a partial dimensional range. Since the minimum distance between the contact surfaces 82 of the intermediate hooks 36, 56 and the contact surfaces 82 of the front end hooks 38, 58, when the intermediate hooks 36, 56 of the individual arms are slid towards the front end hooks 38, 58, is preferably short as possible from the viewpoint of handlability when the rib spreader is attached to the patient. It is appropriate to set the distance, over which the intermediate hooks 36, 56 of the individual arms are slidable (denoted by "L" in FIG. 3), as long as possible without adversely affecting the design. The distance is set typically to 25 to 30 mm for infants, and 50 to 70 mm for adults.

It is appropriate to set the angle of the intermediate bent portions 22, 42 (denoted by "A" in FIG. 3) and the angle of front end bent portions 24, 44 (denoted by "B" in FIG. 3) of the individual arms, based on the curved geometry of the human sternum. A=10° and B=15° are commonly set for infants and adults.

Figure 9:
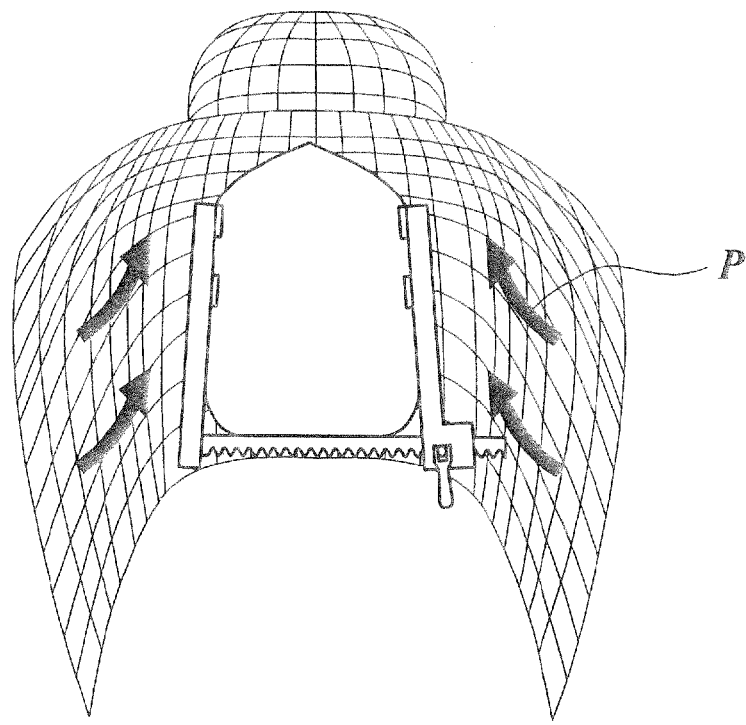
FIG. 9 is a perspective view illustrating a state of displacement of sternum using a conventional rib spreader.
Figure 10:
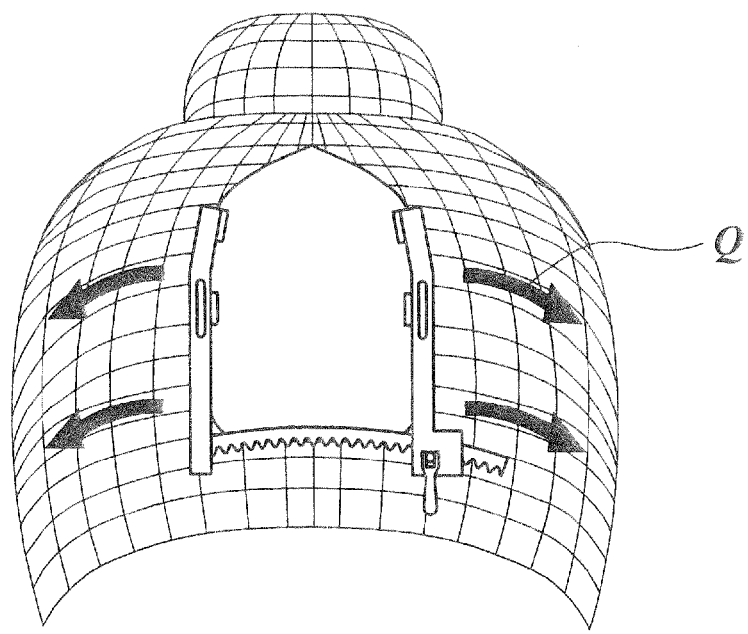
FIG. 10 is a perspective view illustrating a state of displacement of sternum using the rib spreader illustrated in FIG. 1.

FIG. 9 is a perspective view illustrating a state of displacement of sternum using a conventional rib spreader. A force exerted on the human body by the conventional rib spreader having a straight rack contains a component of force P which effects in the direction of bringing the sternum apart from the vertebral column (thoracic vertebra). FIG. 10 is a perspective view illustrating a state of displacement of sternum using the rib spreader illustrated in FIG. 1. A force Q exerted on the human body by the rib spreader of the present invention, having the arch-like curved rack, is a uniform force allowing natural displacement without causing unnatural deformation or concentration of pressure. This is one factor of yielding effects of preventing fracture of sternum, crush of sternum stump, and so forth.

Figure 11:
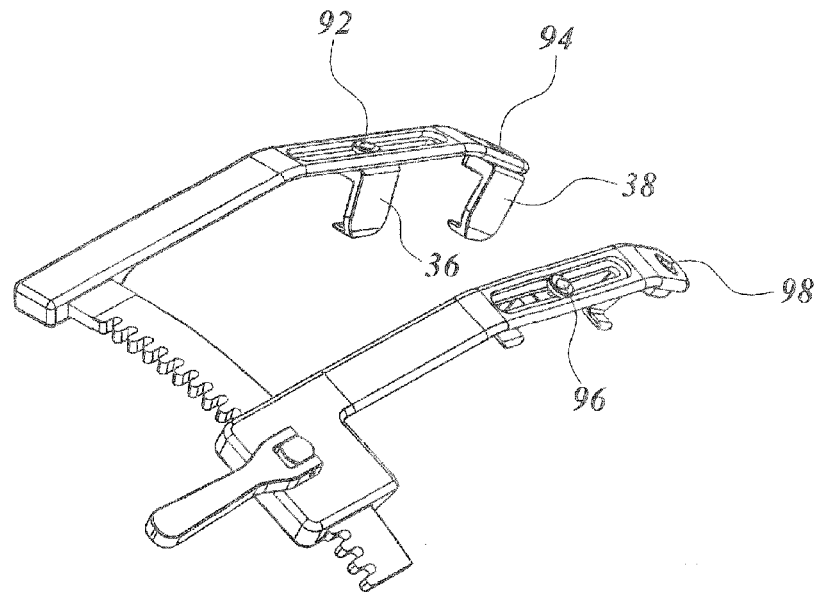
FIG. 11 is a perspective view illustrating a rib spreader according to a second embodiment of the present invention.
Figure 12:
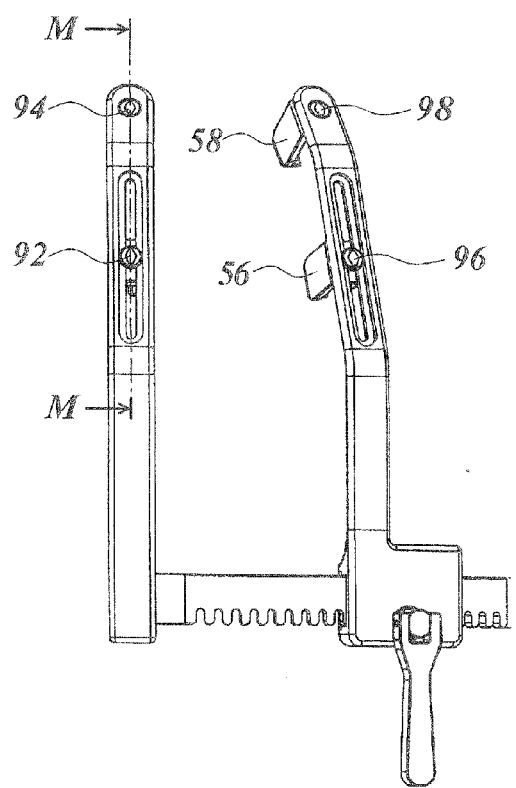
FIG. 12 is a plan view of the rib spreader illustrated in FIG. 11.
Figure 13:
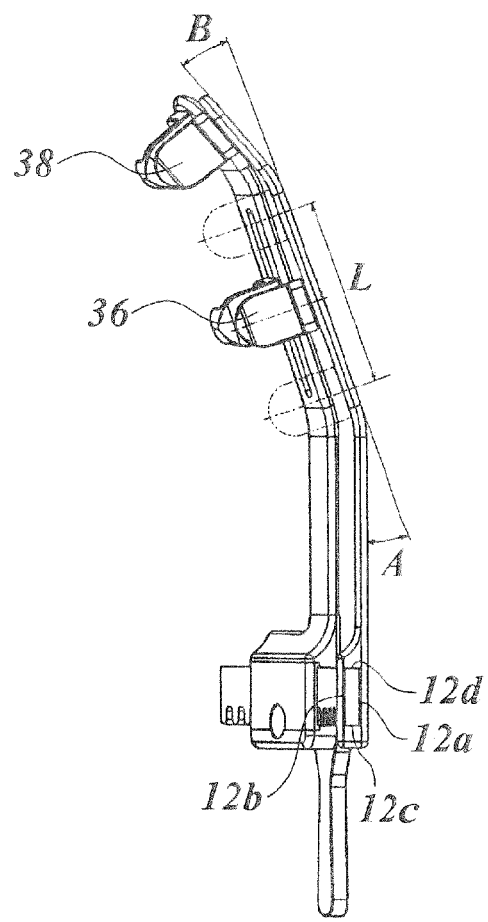
FIG. 13 is a left side elevation of the rib spreader illustrated in FIG. 11.
Figure 14:
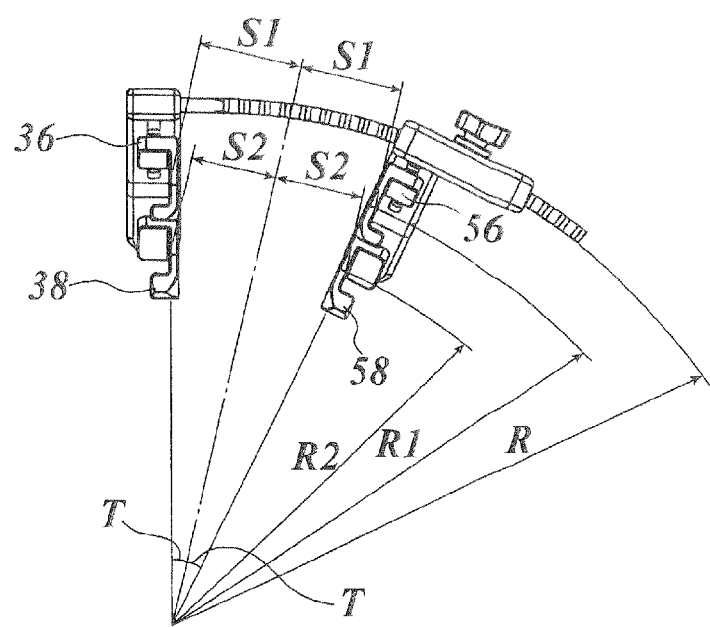
FIG. 14 is a front elevation of the rib spreader illustrated in FIG. 11.

FIG. 11 is a perspective view illustrating a rib spreader according to a second embodiment of the present invention. FIG. 12 is a plan view of the rib spreader illustrated in FIG. 11. FIG. 13 is a left side elevation of the rib spreader illustrated in FIG. 11. FIG. 14 is a front elevation of the rib spreader illustrated in FIG. 11.

In contrast to the rib spreader according to the first embodiment of the present invention, configured so that the nut 80 was fixed to the axial end of the hook stem 76 so as to project out from the top surface of the arm 70, the rib spreader according to the second embodiment of the present invention is improved so as to avoid hooking of surgical suture on the projection.

As seen in FIGS. 11 to 14, axial end caps 92, 96 of the intermediate hooks, and axial end caps 94, 98 of the front end hooks are integrated with the individual nuts 80 on the top surface of the nuts 80.

Figure 15:
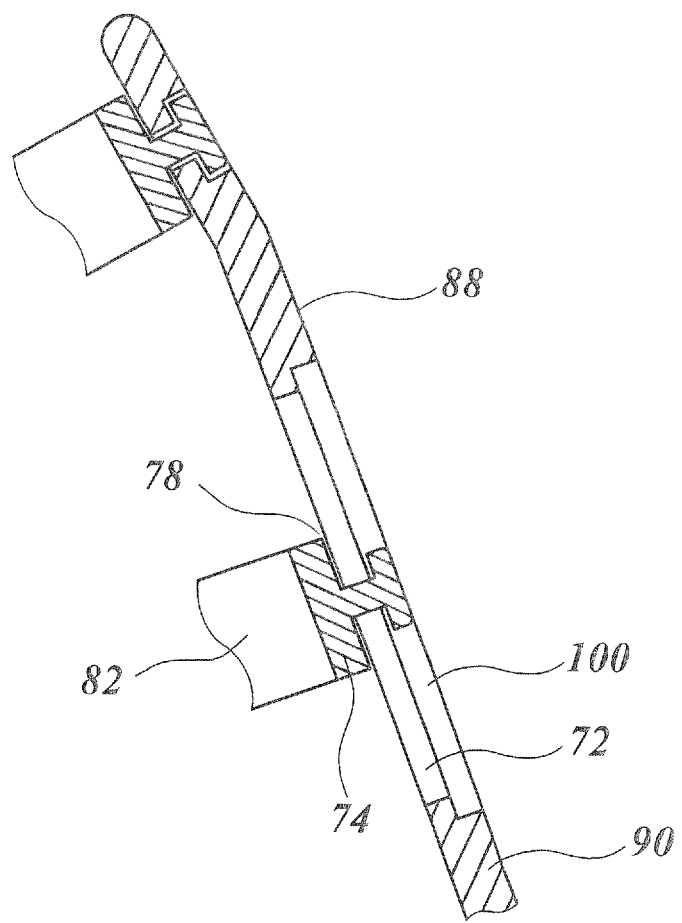
FIG. 15 is a cross sectional view taken along line M-M in FIG. 12.

FIG. 15 is a cross sectional view taken along line M-M in FIG. 12. The hook stem integrated with the hook 74, which corresponds to the intermediate hook 36 of the stationary arm 20, is inserted into the oblong hole 72 of the arm. 90, which corresponds to the oblong hole 32 of the stationary arm 20. The axial end of the hook stem is integrated with the nut. The arm 90 has formed therein an oblong-circular nut insertion recess 100 which accommodates the nut so as not to project it out from the top surface 88 of the arm 90. A style of attachment of the intermediate hook 56 to the movable arm 40 is same as the style of attachment of the intermediate hook 36 to the stationary arm 20. A style of attachment of the front end hook 38 to the stationary arm 20, and a style of attachment of the front end hook 58 to the movable arm 40, are same as the style of attachment of the intermediate hook 36, except that the geometry of the fitting hole is different from that of the oblong hole 72. The level of height of the top surfaces of the individual nuts are lower than that of the top surfaces of the individual arms. Note, however, that since the individual nuts are actually integrated, on the top surfaces thereof, with the axial end caps 92, 96 of the intermediate hook, and the axial end caps of 94, 98 of the front end hooks, so that the level of height of the top surfaces of the individual axial end caps is lower than that of the top surfaces of the individual arms, in a strict sense.

Figure 16:
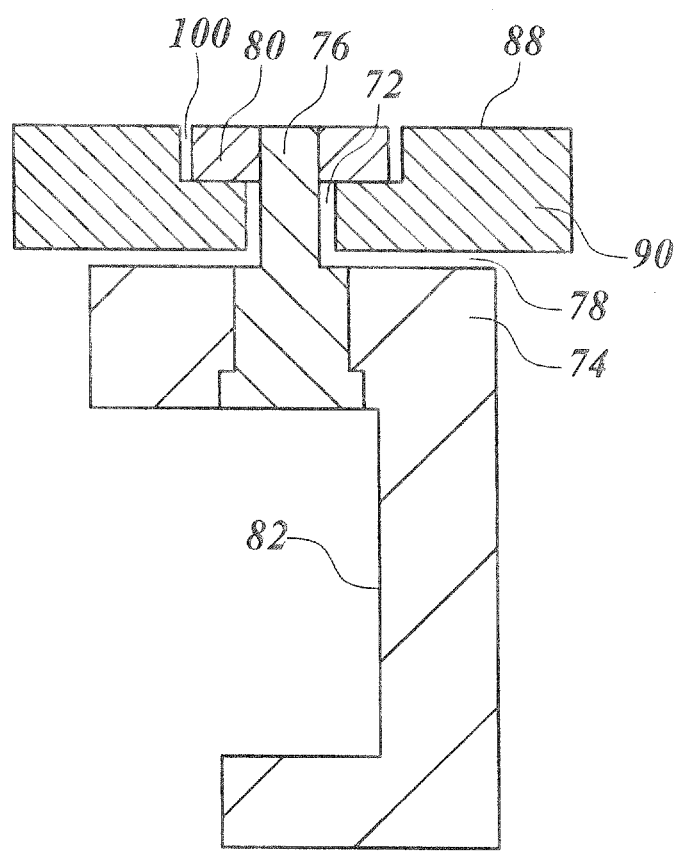
FIG. 16 is a cross sectional view of a fixed structure of the intermediate hook illustrated in FIG. 12.

FIG. 16 is a cross sectional view illustrating a fixed structure of the intermediate hook illustrated in FIG. 12, taken along a line drawn laterally in FIG. 12 through the center of the axial end cap 92 of the intermediate hook. The hook stem 76 fixed to the hook 74, which corresponds to the intermediate hook 36 of the stationary arm 20, is inserted into the oblong hole 72 of the arm 90, which corresponds to the oblong hole 32 of the stationary arm 20. The nut 80 with the axial end cap 92 (not illustrated) of intermediate hook is engaged with the axial end of the hook stem 76 so as not to project it out from the top surface 88 of the arm 90. Similarly to the rib spreader according to the first embodiment of the present invention, there is a gap 78 between the arm 90 and the hook 74 so as to keep the hook 74 slidable and pivotable, and there is also a gap between the flat portions of the side face of the oblong hole 72 and the flat portions of the hook stem 76 so as to keep the hook 74 slidable and pivotable. While FIG. 16 illustrates a style of fixation of the intermediate hook 36 to the stationary arm 20, the style of fixation of the intermediate hook 56 to the movable arm 40 may be the same except that the direction of facing of the contact surface 82 will be opposite.

The configurations of the first embodiment illustrated in FIGS. 5 and 6 are also adoptable to the rib spreader according to the second embodiment of the present invention. More specifically, the hook stem 76 has, in portions of the side face thereof, two nearly-parallel flat surfaces formed by milling, so as to make the hook 74 slidable in the oblong hole 72, by setting the width of the oblong hole 72 smaller than the distance between these two surfaces, and so as to make the hook 74 pivotable only within a predetermined angular range, by setting the width of the oblong hole 72 smaller than the maximum diameter of the hook stem 76.

Similarly to the rib spreader according to the first embodiment of the present invention, also in the rib spreader according to the second embodiment, it is not necessary for the front end hook 38 of the stationary arm 20 and the front end hook 58 of the movable arm 40 to be slidable. Accordingly, the hook stem 76 fixed to the hook 74 is inserted respectively in a hole provided to the front end portion 30 of the stationary arm 20 and in a hole provided to the front end portion 50 of the movable arm 40, which are provided so as to allow therein pivoting only. The arm 90 has a circular nut insertion recess formed therein. Each nut 80 with the axial end cap 94 or 98 (not illustrated) of front end hook is engaged with the axial end of the hook stem 76 so as not to project out from the top surface 88 of the arm 90. Each of the holes is functionally an oblong hole which allows therein no slidable distance for the hook 74, and is, more strictly, a hole with a geometry derived from a circle with the exception of two segments divided by two nearly-parallel chords. The gap 78, which allows therein pivoting of the hook 74, is provided between the arm 70 and the hook 74, and also a gap, which allows therein pivoting of the hook 74, is again provided between each of the flat portions of the side faces of the individual holes, and the flat portions of the hook stem 76. The pivoting of the hook 74 is restricted to a predetermined angle, by adjusting the distance between the flat portions of the side faces of the individual holes smaller than the maximum diameter of the hook stem 76.

In FIG. 14, R denotes the radius of curvature of the rack which curves archwise along a cylindrical surface; R1 denotes the distance between the center of curvature of the rack and the contact surfaces of the intermediate hooks 36, 56; R2 denotes the distance between the center of curvature of the rack and the contact surfaces of the front end hooks 38, 58; S1 denotes a half of the distance between the contact surfaces of the intermediate hooks 36, 56; S2 denotes a half of the distance between the contact surfaces of the front end hooks 38, 58; and T denotes a half of the relative angle of inclination of the contact surfaces. Since relations of $R1=S1/\sin(T)$, and $R2=S2/\sin(T)$ hold, then R1 and R2 may be determined if S1, S2 and T are empirically obtained. In addition, if the difference between R and R1, and the difference between R and R2 are determined on the drawing, R may be determined by respectively adding these differences to R1 and R2.

In other words, the radius of curvature R of the rack which curves archwise along a cylindrical surface may appropriately be determined based on the distance (at least one of S1 and S2) between the left and right contact surfaces measured when the human sternum is displaced towards the left and right, and the angle of inclination of contact surface (T). The radius of curvature R is typically set to 120 mm for the rib spreader for infants, and 184 mm for adults.

The maximum angular range over which the contact surfaces of the individual hooks are pivotable about the individual arms is preferably ±15° or larger and ±45° or smaller, and more preferably ±25° or larger and ±35° or smaller. The distance over which the intermediate hooks 36, 56 of the individual arms are slidable (denoted by "L" in FIG. 13) is set to 25 to 27 mm for the rib spacers for infants, and 40 to 70 mm for adults.

The angle of the intermediate bent portions 22, 42 of the individual arms (denoted by "A" in FIG. 13) and the angle of the front end bent portions 24, 44 (denoted by "B" in FIG. 13) are set to A=20° and B=20°, commonly for both of infants and adults.

The rib spreaders according to the first and second embodiments of the present invention are excellent in terms of preventing fracture of sternum and crush of sternum stump, and in terms of absorbing personal differences in the length of sternum of patients or state of deformation of sternum during displacement, but are still insufficient in terms of ensuring a good field of view and a sufficient working area for surgery. This is because the stationary arm 20 having the bent portions and the movable arm 40 having the bent portions are directly coupled with the rack 12 which curves archwise along a cylindrical surface, so that the distance between the contact surfaces of the front end hooks 38, 58 becomes shorter than the distance between the contact surfaces of the intermediate hooks 36, 56, as the distance of displacement of sternum increases. This makes the upper portion of heart less readily recognizable as a consequence. The rib spreaders of the third and fourth embodiments, directed to solve these problems, will be explained in the next.

Figure 17:
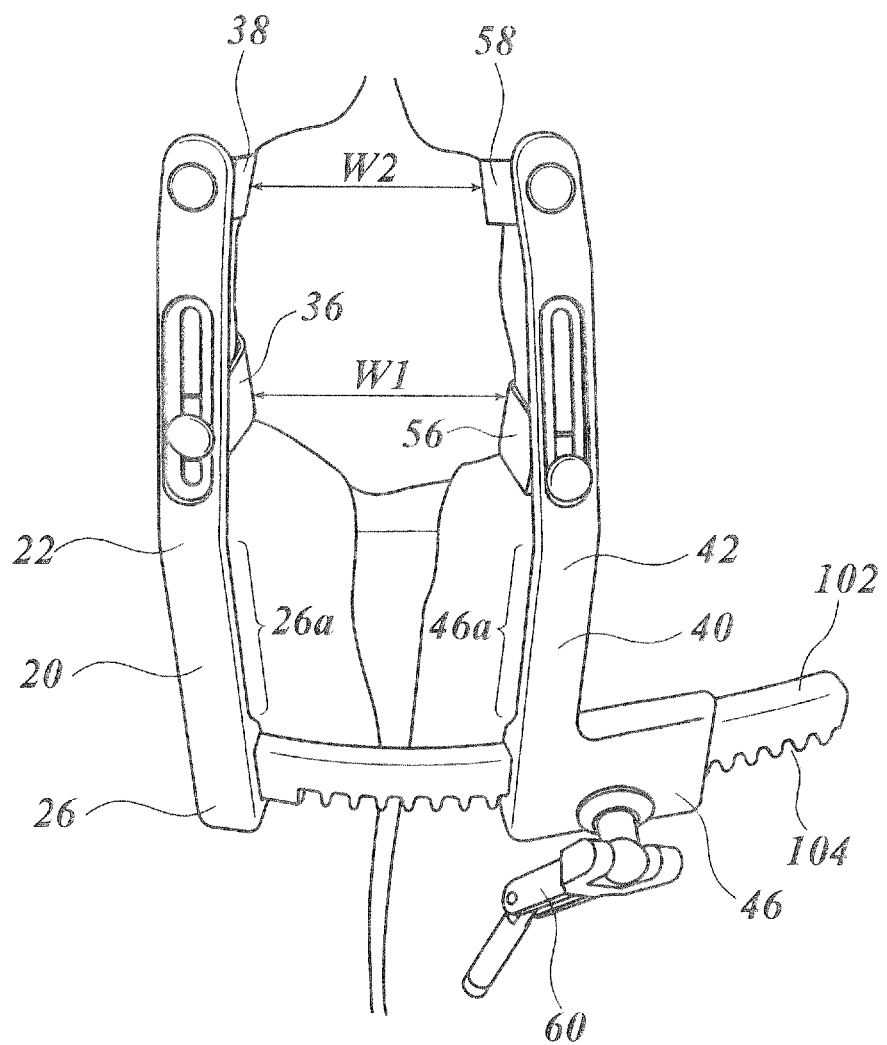
FIG. 17 is a perspective view illustrating a state of displacement of sternum using a rib spreader according to a third embodiment of the present invention.

FIG. 17 is a perspective view illustrating a state of displacement of sternum using the rib spreader according to the third embodiment of the present invention. 26a denotes a front end-side straight portion of the base end 26 of the stationary arm 20. 46a denotes front end-side straight portion of the base end 46 of the movable arm 40. In the rib spreaders according to the first and second embodiments of the present invention, the front end-side straight portion 26a of the base end 26 and the front end-side straight portion 46a of the base end 46 were kept in parallel irrespective of position of the movable arm 40. Accordingly, the distance W2 between the contact surfaces of the front end hooks 38, 58 was always shorter than the distance W1 between the contact surfaces of the intermediate hooks 36, 56. In contrast, in the rib spreader according to the third embodiment of the present invention, the angle of the front end-side straight portion 46a of the base end 46 relative to the front end-side straight portion 26a of the base end 26 is adjustable based on position of the movable arm 40. Accordingly, the distance W2 between the contact surfaces of the front end hooks 38, 58 may be made equal to the distance W1 between the contact surfaces of the intermediate hooks 36, 56.

Figure 18A:
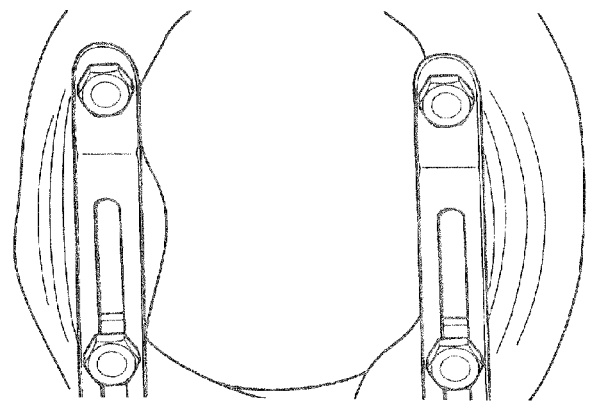
FIG. 18A is a perspective view illustrating a state of displacement of sternum using a conventional rib spreader.
Figure 18B:
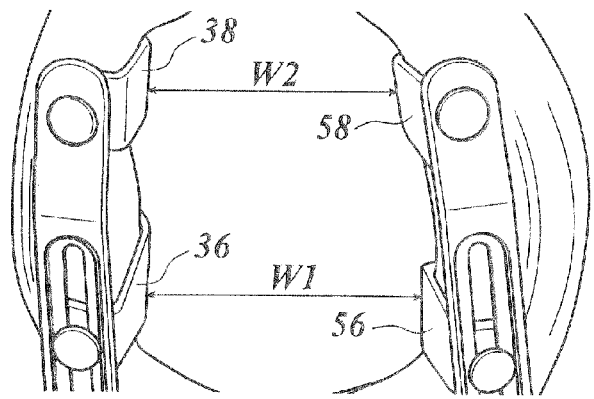
FIG. 18B is a perspective view illustrating a state of displacement of sternum using the rib spreader according to the second embodiment of the present invention.
Figure 18C:
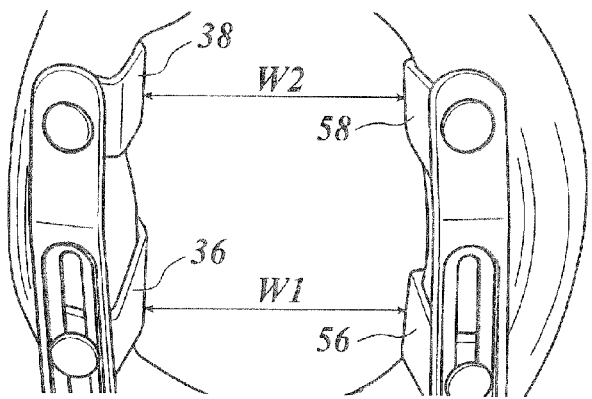
FIG. 18C is a perspective view illustrating a state of displacement of sternum using the rib spreader according to the third embodiment of the present invention.

FIG. 18A is a perspective view illustrating a state of displacement of sternum using the conventional rib spreader having a straight rack, wherein the width of displacement at the intermediate portion equals to the width of displacement at the front end portion. The stationary arm and the movable arm, however, overhang the hooks at both end portions of the displaced area. This considerably degrades the operability in these portions. FIG. 18B is a perspective view illustrating a state of displacement of sternum using the rib spreader according to the second embodiment of the present invention, wherein the stationary arm and the movable arm do not overhang the hooks at both end portions of the displaced area. But the upper portion of the heart is not fully recognizable since the distance W2 between the contact surfaces of the end hooks 38, 58 is shorter than the distance W1 between the contact surfaces of the intermediate hooks 36, 56. FIG. 18C is a perspective view illustrating a state of displacement of sternum using the rib spreader according to the third embodiment of the present invention, wherein the stationary arm and the movable arm do not overhang the hooks at both end portions of the displaced area, and distance W2 between the contact surfaces of the front end hooks 38, 58 is nearly equal to the distance W1 between the contact surfaces of the intermediate hooks 36, 56. That makes the upper portion of heart more readily recognizable. In short, the configuration ensures a good field of view and a sufficient working area for surgery, and a good operability.

Figure 19:
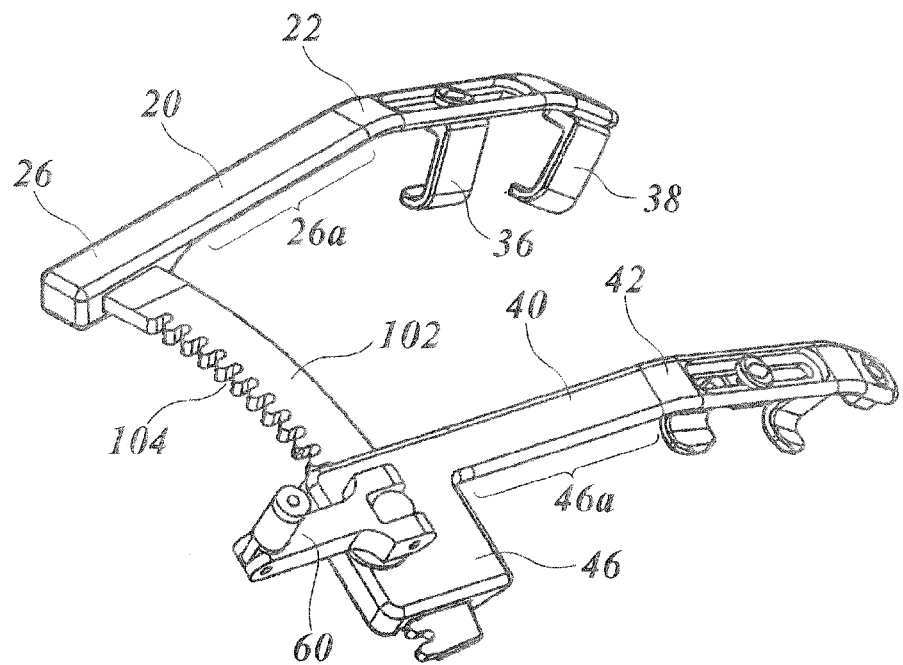
FIG. 19 is a perspective view illustrating the rib spreader according to the third embodiment of the present invention.
Figure 20:
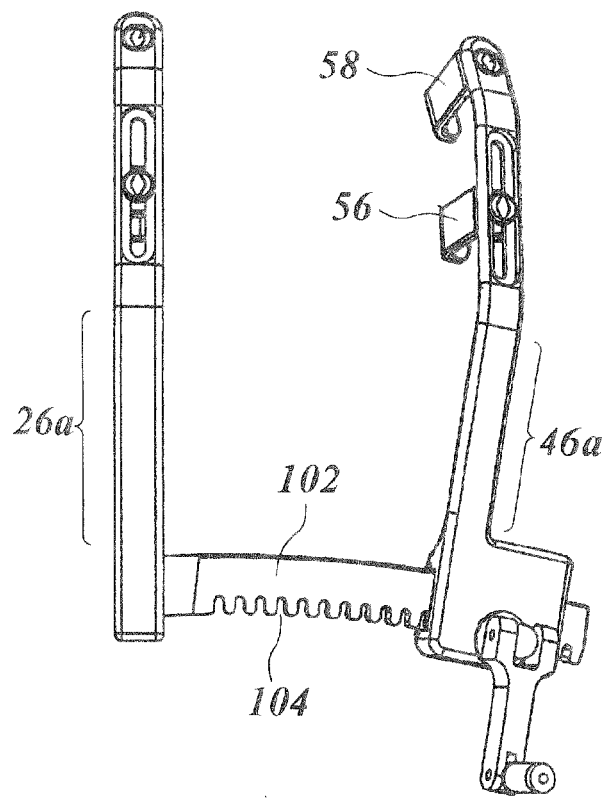
FIG. 20 is a plan view of the rib spreader illustrated in FIG. 19.
Figure 21:
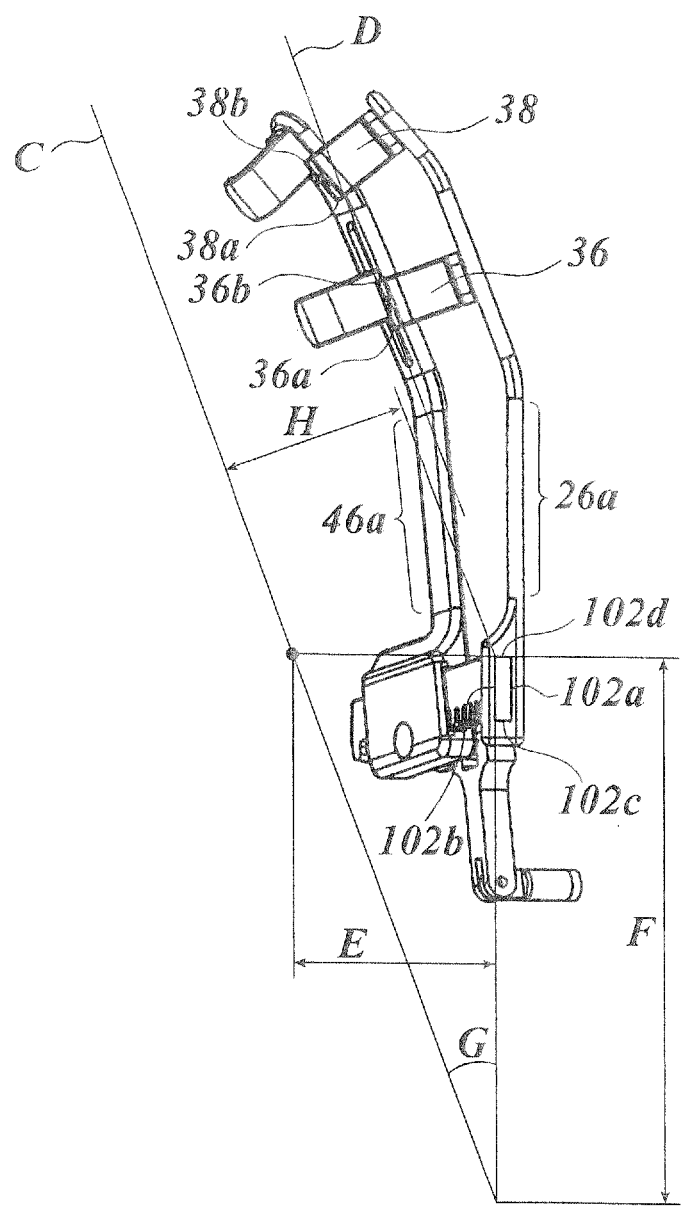
FIG. 21 is a left side elevation of the rib spreader illustrated in FIG. 19.
Figure 22:
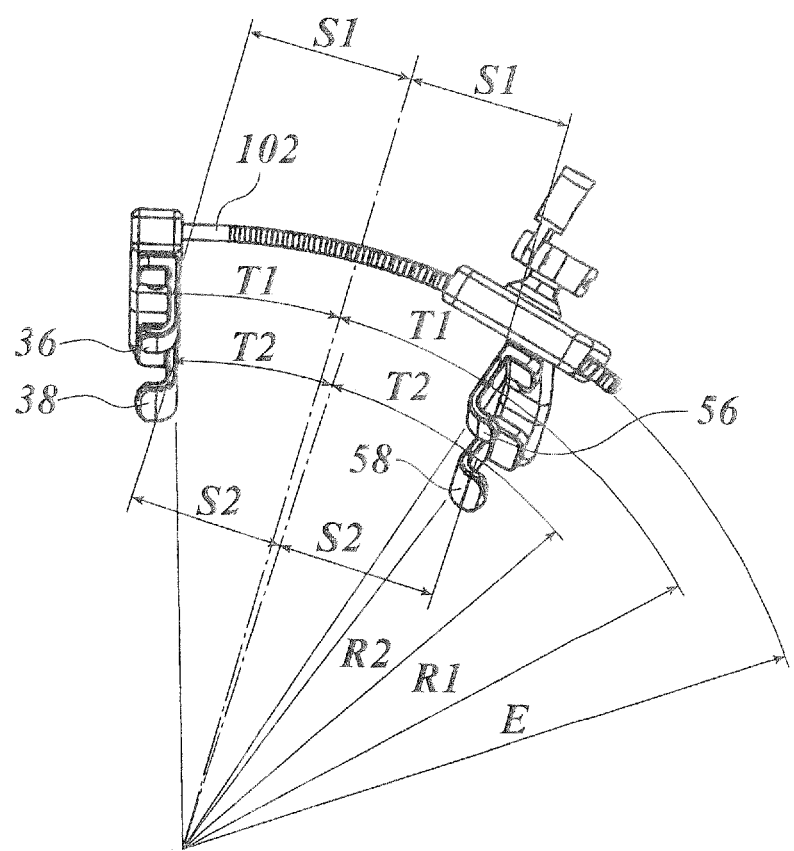
FIG. 22 is a front elevation of the rib spreader illustrated in FIG. 19.

FIG. 19 is a perspective view illustrating the rib spreader according to the third embodiment of the present invention; FIG. 20 is a plan view of the rib spreader illustrated in FIG. 19; FIG. 21 is a left side elevation of the rib spreader illustrated in FIG. 19; and FIG. 22 is a front elevation of the rib spreader illustrated in FIG. 19.

As described in the above, the upper portion of heart was less readily recognizable when the rib spreaders according to the first and second embodiments of the present invention were used. But the rib spreader according to the third embodiment of the present invention was improved in the insufficient aspects regarding the field of view and operability, by using a rack 102 in place of the rack 12. In short, the rib spreader according to the second embodiment of the present invention and the rib spreader according to the third embodiment of the present invention are different in that which of the rack 12 and the rack 102 is used, and in that whether a good field of view and sufficient working area, and a good operability may be ensured or not. The other aspects are the same in the both rib spreaders.

As illustrated in FIG. 3 and FIG. 13, the rack 12 of the rib spreader according to the first and second embodiments of the present invention curves archwise, just like given in a form of partial hollow cylinder. In other words, the rack 12 has a rectangular cross section taken normal to the longitudinal direction thereof, and two side faces 12a, 12b corresponding to two long edges of the rectangle curve archwise along two concentrically-arranged cylindrical surfaces. On the other hand, two side faces 12c, 12d which correspond to two short edges of the rectangle are arranged concentrically around the same center axis but respectively normal to the two cylindrical surfaces. One of the two side faces, typically the side face 12c, has teeth 14 which allow the movable arm 40 to move along the teeth 14.

In contrast, as illustrated in FIG. 21, the rack 102 of the rib spreader according to the third embodiment of the present invention curves archwise, just like given in a form of partial hollow cone. In other words, the rack 102 has a rectangular cross section taken normal to the longitudinal direction thereof, and two side faces 102a, 102b corresponding to two long edges of the rectangle curve archwise along two first conical surfaces which have predetermined conical angles G assumed around the same center axis C. On the other hand, two side faces 102c, 102d which correspond to two short edges of the rectangle are curved archwise along two second conical surfaces which have the same center axis C but respectively aligned normal to the two first conical surfaces.

In other words, the two side faces 102c, 102d are two curved surfaces respectively curved along two second conical surfaces assumed around the same center axis C. One of the two curved surfaces which respectively curve along the two second conical surfaces (two side faces 102c, 102d), typically the side face 102c, has teeth 104 which allow the movable arm 40 to move along the teeth 104.

By using the rack 102, the movable arm 40 moves around center axis C, along the conical surface having a predetermined conical angle around the center axis C. Now in the cross section of the rack 102 taken normal to the longitudinal direction thereof, an intersection formed by the long edges 102b and short edges 102d, which is on the front end side of the arm and closer to the center axis C out of four apexes of the rectangular cross section, is assumed as a reference point. "H" denotes the radius of curvature at the reference point. In an ellipse obtained by projecting a circular locus given by the reference point which moves around the center axis C onto a front elevation (FIG. 22), "E" denotes the longest radius of curvature which resides on the short axis of the ellipse. In an ellipse obtained by projecting the circular locus onto a plan view (FIG. 20), "F" is the longest radius of curvature which resides on the short axis of the ellipse.

In FIG. 21, 36a denotes a base end-side apex of the intermediate hook 36; 36b denotes a front end-side apex of the intermediate hook 36; 38a denotes a base end-side apex of the front end hook 38; and 38b denotes a front end-side apex of the front end hook. Line D parallel to the center axis C is now drawn through the apex 36a which resides closest to the rack 102 out of these four apexes. It is now understood that the apex 38b and the apex 38a fall beyond (leftward in the drawing) the parallel line D towards the center line C. This means that the radii of curvature at the apex 38b and the apex 38a are shorter than the radius of curvature at the apex 36a, and also means that, in the displacement of sternum, the distance W2 between the contact surfaces of the front end hooks 38, 58 will be shorter than the distance W1 between the contact surfaces of the intermediate hooks 36, 56.

Figure 23:
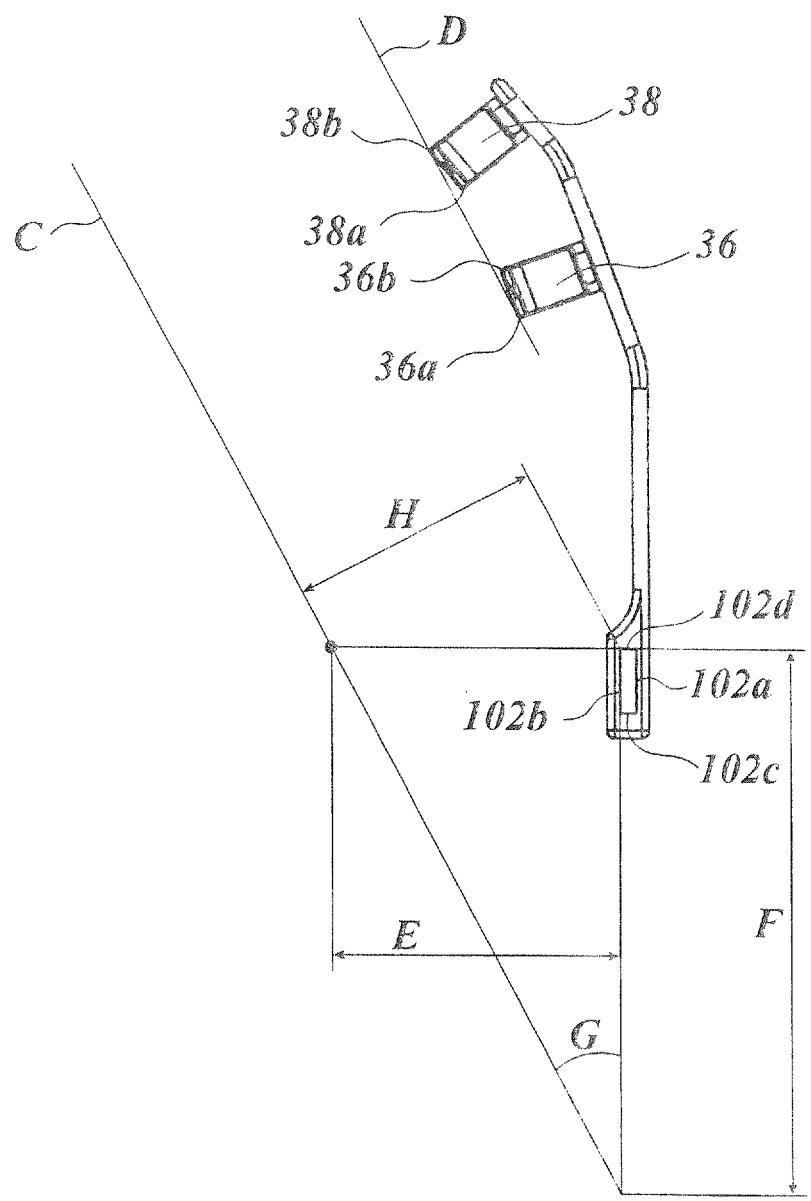
FIG. 23 is a left side elevation supplementarily explaining FIG. 21.

In the example illustrated in FIGS. 19 to 22, the distance W1 between the contact surfaces of the intermediate hooks 36, 56 was not equal to the distance W2 between the contact surfaces of the front end hooks 38, 58, since a conical angle G was set to same as angle A(20°) of the intermediate bent portions 22, 42 illustrated in FIG. 13. It is now possible to make the distance W1 between the contact surfaces of the intermediate hooks 36, 56 equal to the distance W2 between the contact surfaces of the front end hooks 38, 58, by drawing, as illustrated in FIG. 23, the center axis C in parallel to the parallel line D which passes through the apex 36a and the apex 38b, and by determining the conical angle G away from the center axis C. While FIG. 23 illustrates a conical angle G of approximately 27°, it may be set to 25 to 30° commonly for both of infants and adults.

Alternatively, as illustrated in FIG. 22, the longest radius of curvature, on the short axis of an ellipse projected on the front elevation (FIG. 22), of the rack 102 which curves archwise along a conical surface having a predetermined conical angle, may be determined in an approximated manner, based on the distance between the left and right contact surfaces (at least either one of S1 and S2) and the angle of inclination of the contact surfaces (at least either one of T1 and T2) when the human sternum is displaced laterally, similarly to the case of using the rib spreaders according to the first and second embodiments of the present invention. The reason why the "approximation" is allowable herein is that the conical angle G is not larger than 30°, so that the ellipse projected on the front elevation (FIG. 22) of the rack 102 shows only a small difference between the short axis and the long axis. Since equations of $R1=S1/\sin(T1)$ and $R2=S2/\sin(T2)$ hold, $R1$ and $R2$ may be determined if $S1$, $S2$, and $T1$, $T2$ are empirically obtained. In addition, if the difference between E and R1, and the difference between E and R2 are determined on the drawing, E may be determined by respectively adding these differences to R1 and R2.

Figure 24:
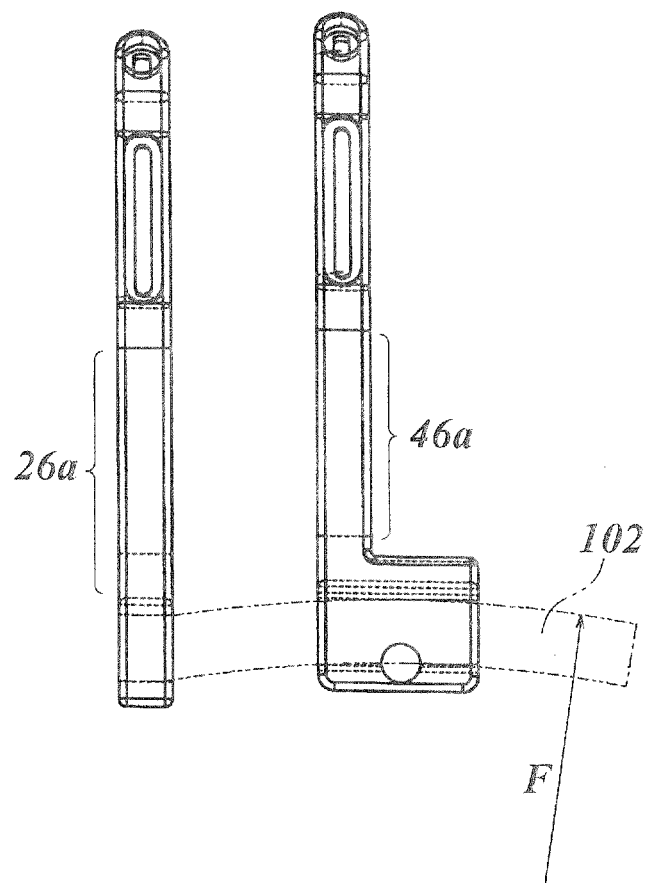
FIG. 24 is a plan view of a state of development of the rack illustrated in FIG. 19.

FIG. 24 is a is a plan view illustrating a state of development, into a plane, of the rack illustrated in FIG. 19, which curves archwise along a conical surface having a predetermined conical angle. If the rack 102 is curved by metal stamping, the rack 102 is necessarily cut in a form indicated by two-dot chain line in FIG. 24.

Figure 25:
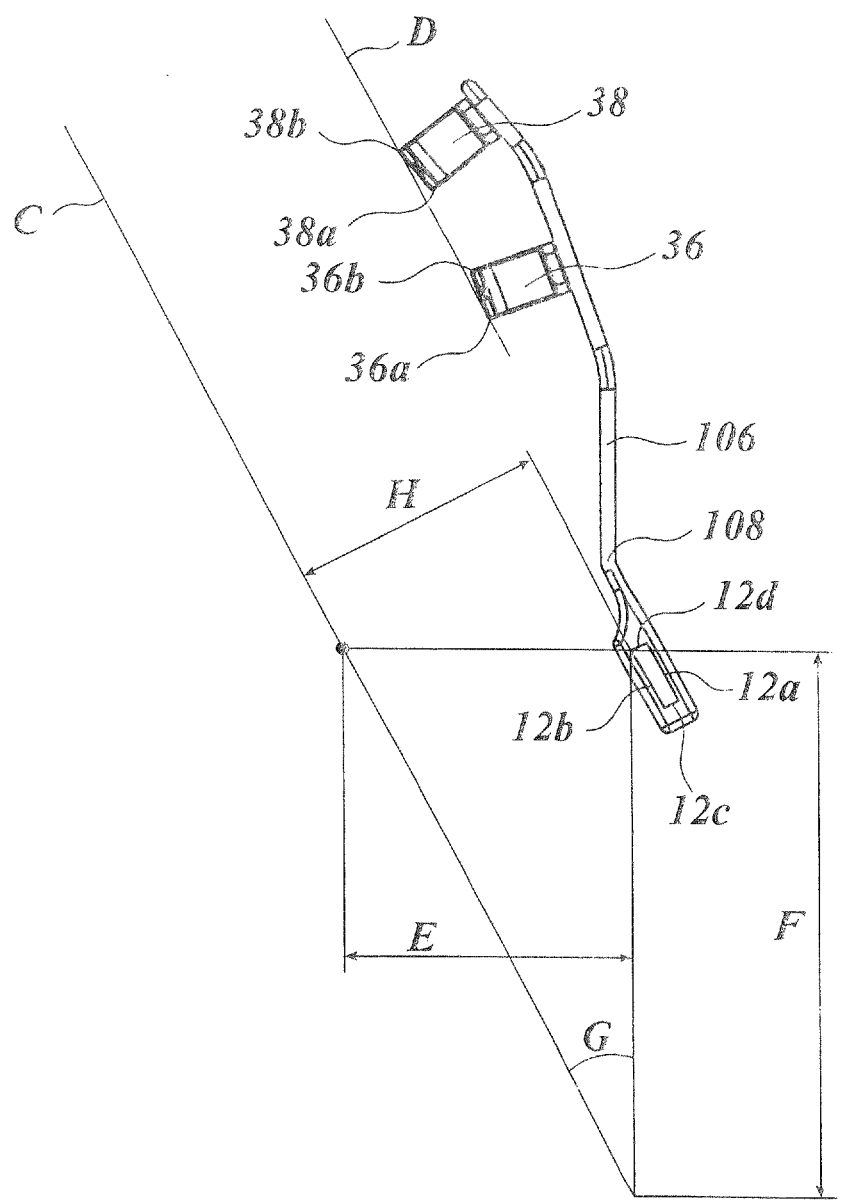
FIG. 25 is a left side elevation illustrating a rib spreader according to a fourth embodiment of the present invention.

FIG. 25 is a left side elevation illustrating the rib spreader according to the fourth embodiment of the present invention. As described in the above, the rib spreader according to the third embodiment of the present invention used the rack which curved archwise along a conical surface having a predetermined conical angle, in order to improve inferiority in the field of view and working area for surgery, and in the operability.

On the other hand, in the rib spreader according to the fourth embodiment of the present invention, the base end of the stationary arm 106 has a base end bent portion 108 which bends in the direction opposite to the intermediate bent portion 22 and the front end bent portion 24, by an angle same as the conical angle G in the rib spreader according to the third embodiment of the present invention, wherein an unillustrated movable arm, having the same geometry with the stationary arm 106, moves along the cylindrical surface of the rack 12 which curves archwise along the cylindrical surface, and around the center axis C. Now in the cross section of the rack 12 taken normal to the longitudinal direction thereof, an intersection formed by the long edges 12b and short edges 12d, which is on the front end side of the arm and closer to the center axis C out of four apexes of the rectangular cross section, is assumed as a reference point. "H" denotes the radius of curvature at the reference point.

The rib spreader according to the third embodiment of the present invention and the rib spreader according to the fourth embodiment of the present invention are different in that which of the rack 12 as a part of cylindrical surface and the rack 102 as a part of conical surface having a predetermined conical angle, is used as the rack which curves archwise; and in that whether the stationary arm and the movable arm have the base end bent portion 108 or not. The both are the same in the other aspects.

Figure 26:
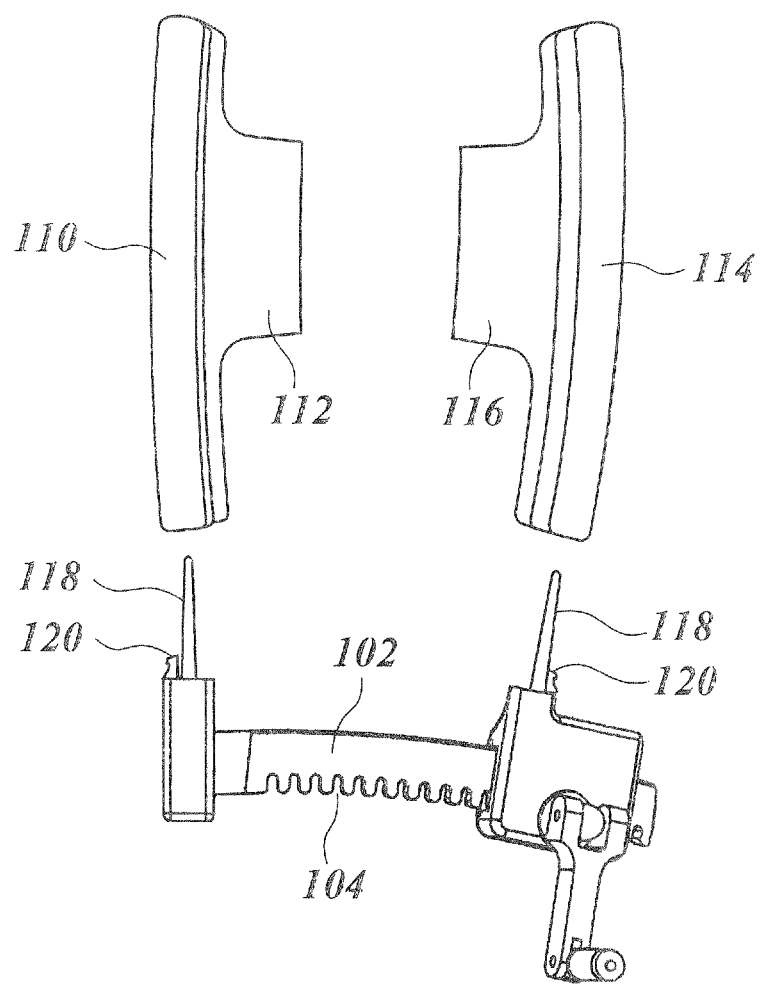
FIG. 26 is a plan view illustrating a rib spreader according to a fifth embodiment of the present invention.

FIG. 26 is a plan view illustrating the rib spreader according to the fifth embodiment of the present invention, wherein a detachable unit is provided to each of the stationary arm and the movable arm, so as to fix the front end-side portions of the stationary arm and the movable arm, in a detachable manner. Shown herein is a disassembled state of the rib spreader according to the third embodiment illustrated in FIGS. 19-22, from which the stationary arm 20 and the movable arm 40 each having two hooks 36, 38 and two hooks 56, 58 have been detached respectively from the individual detachable units, but instead in preparation of attachment of a replacement stationary arm 110 having one hook 112, and a replacement movable arm 114 having one hook 116.

When the fifth embodiment of the present invention is applied to the rib spreader according to the third embodiment of the present invention, it is preferable to provide the detachable units to the front end-side straight portions 26a, 46a at the base ends of the stationary arm and the movable arm. The same position is preferable also for the case where the fifth embodiment of the present invention is applied to the rib spreader according to the fourth embodiment of the present invention, wherein both of the front end-side and the base end-side of the base end bent portion 108 illustrated in FIG. 25 are allowable. The detachable unit herein has a positioning pin 118 and a lock mechanism 120, so as to allow easy attachment/detachment, without loosening.

Having detailed the rib spreader of the present invention, it is obvious that the present invention is not limited by the embodiments described in the above, and that various improvements and modifications may be made without departing from the purport of the present invention.

INDUSTRIAL APPLICABILITY

As described in the above, according to the preferable embodiments of the present invention, any unnatural deformation in the process of displacement of sternum is avoidable, by making the rack curved archwise. Any difference in stress exerted on the contact surfaces between the portions distant from the human body and closer to the human body may be reduced, by configuring the rib spreader so that the incision planes of sternum and the contact surfaces of the individual hooks are kept in surface contact, conforming to changes in the angle of incision planes of sternum. Accordingly, fracture of sternum and crush of sternum stump are avoidable.

Accordingly, the present invention is preferably adoptable in particular to a technique directed to prevent fracture of sternum or crush of sternum stump in the process of displacement of sternum after median sternotomy, by displacing the sternum using a rib spreader naturally by an uniform force without causing unnatural deformation or concentration of pressure; directed to absorb personal differences in the length of sternum of patients, or the state of deformation of sternum during displacement; and also directed to ensure a good field of view and a sufficient working area for surgery, and to ensure a good operability and flexibility of adoption.

EXPLANATION OF THE MARKS 10 rib spreader
12 rack
12a, 12b long edge of rectangular cross section of rack
12c, 12d short edge of rectangular cross section of rack
14 teeth
20 stationary arm
22 intermediate bent portion
24 front end bent portion
26 base end
26a front end-side straight portion
28 intermediate portion
30 front end portion
32 oblong hole
34 hole
36 intermediate hook
36a base end-side apex of intermediate hook
36b front end-side apex of intermediate hook
38 front end hook
38a base end-side apex of front end hook
38b front end-side apex of front end hook
40 movable arm
42 intermediate bent portion
44 front end bent portion
46 base end
46a front end-side straight portion
48 intermediate portion
50 front end portion
52 oblong hole
54 hole
56 intermediate hook
58 front end hook
60 handle
70 arm 72 oblong hole
74 hook
76 hook stem
78 gap
80 nut
82 contact surface
84 pin
86 gap
88 top surface
90 stationary arm
92 axial end cap of intermediate hook
94 axial end cap of front end hook
96 axial end cap of intermediate hook
98 axial end cap of front end hook
100 nut insertion recess
102 rack
102a, 102b long edge of rectangular cross section of rack
102c, 102d short edge of rectangular cross section of rack
104 teeth
106 stationary arm
108 base end bent portion
A angle of intermediate bent portion
B angle of front end bent portion
C center axis of rack
D parallel line with center axis of rack
E longest radius of curvature on short axis of ellipse projected on front elevation (FIG. 22) of rack
F longest radius of curvature on short axis of ellipse projected on plan view (FIG. 20) of rack
G conical angle of rack
H radius of curvature of rack
L slidable distance of intermediate hook
P force exerted by conventional rib spreader
Q force exerted by inventive rib spreader
R radius of curvature of rack
R1 distance between center of curvature of rack and contact surface of intermediate hook
R2 distance between center of curvature of rack and contact surface of front end hook
S1 (distance between contact surfaces of intermediate hooks)/2
S2 (distance between contact surfaces of front end hooks)/2
T angle of inclination of contact surface
T1 angle of inclination of contact surface of intermediate hook
T2 angle of inclination of contact surface of front end hook
W1 distance between contact surfaces of intermediate hooks
W2 distance between contact surfaces of front end hooks

What is claimed is:

1. A rib spreader comprising:
a stationary arm having a first bent portion;
at least one first hook system attached to the stationary arm distal to the first bent portion, wherein the at least one first hook system comprises a first hook and a third hook arranged along a longitudinal direction of the stationary arm distal to the first bent portion and attached so as to be pivotable over a predetermined angular range, the third hook being distal to the first hook and nearer a front end-side of the stationary arm, and each of the first hook and the third hook having a contact surface to be brought into contact with one of two incision planes of a sternum of a human body;
a rack which is fixed to a base end of the stationary arm at a predetermined angle;
a movable arm which has a second bent portion, and which is supported at a base end thereof by the rack so as to be movable along the rack, to thereby vary a distance from the stationary arm; and
at least one second hook system attached to the movable arm distal to the second bent portion, wherein the at least one second hook system comprises a second hook and a fourth hook arranged along a longitudinal direction of the movable arm distal to the second bent portion and attached so as to be pivotable over a predetermined angular range, the fourth hook being distal to the second hook and nearer a front end-side of the movable arm, and each of the second hook and the fourth hook having a contact surface to be brought into contact with the other one of the two incision planes;
wherein the rack is curved archwise as a partial hollow cone, and the rack has:
a rectangular cross section normal to a longitudinal direction of the rack along which the movable arm moves;
two first side faces corresponding to two long edges of the rectangular cross section, said two first side faces being curved along two conical surfaces each forming a predetermined angle with a same center axis passing through apexes of the respective conical surfaces, one of the two first side faces facing a side of the human body and the other facing an opposite side when the rib spreader is attached to the sternum; and
two second side faces corresponding to two short edges of the rectangular cross section, said two second side faces being normal to the two first side faces, having shorter widths than widths of the two first side faces, and being curved along two curved surfaces normal to the two conical surfaces, wherein one of the two second side faces has teeth along which the movable arm moves;
wherein the predetermined angles formed by the center axis and the two conical surfaces are set so that a distance between the contact surface of the first hook and the contact surface of the second hook, is made nearly equal to a distance between the contact surface of the third hook and the contact surface of the fourth hook; and
wherein the center axis is parallel to a line passing through a base end-side apex of the contact surface of the first hook and a front end-side apex of the contact surface of the third hook, and a line passing through a base end-side apex of the contact surface of the second hook and a front end-side apex of the contact surface of the fourth hook.

2. The rib spreader of claim 1, wherein a radius of curvature of the rack, measured at a predetermined position thereof away from the center axis, is determined by a predetermined calculation based on the distance between the contact surface of the first hook and the contact surface of the second hook and an angle formed by the two contact surfaces, the distance and the angle being observed when the rib spreader is attached to laterally displace the sternum of the human body.

3. The rib spreader of claim 1, wherein:
the stationary arm has a third bent portion distal to the first bent portion, the first hook is engaged with a first oblong hole, which is provided between the first bent portion and the third bent portion of the stationary arm, and is oblong in the longitudinal direction of the stationary arm, such that the first hook is slidable therein and pivotable over the predetermined angular range, the stationary arm further has a first front end hole which is provided distal to the third bent portion, the third hook engages with the first front end hole so as to be pivotable over the predetermined angular range, the movable arm has a fourth bent portion distal to the second bent portion, the second hook is engaged with a second oblong hole, which is provided between the second bent portion and the fourth bent portion of the movable arm, such that the second hook is slidable therein and pivotable over the predetermined angular range, the movable arm further has a second front end hole which is provided distal to the fourth bent portion, and the fourth hook engages with the second front end hole so as to be pivotable over the predetermined angular range.

4. The rib spreader of claim 3, wherein a bend angle of the first and second bent portions, and a bend angle of the third and fourth bent portions are respectively set based on a curved geometry of the sternum of the human body.

5. The rib spreader of claim 3, wherein a maximum distance between the contact surface of the first hook and the contact surface of the third hook, and a maximum distance between the contact surface of the second hook and the contact surface of the fourth hook, are set based on a length of the sternum of the human body.

6. The rib spreader of claim 3, wherein a maximum angular range over which the respective contact surfaces of the first hook and the third hook are pivotable about the stationary arm, and a maximum angular range over which the respective contact surfaces of the second hook and the fourth hook are pivotable about the movable arm, are each from approximately 25 to 35 degrees.

7. The rib spreader of claim 3, wherein:

respective first fixing nuts with which the first hook and the third hook are respectively engaged to the first oblong hole and the first front end hole of the stationary arm, are embedded into the stationary arm, so as to align top surfaces of the respective first fixing nuts to a level not exceeding that of a top surface of the stationary arm, and respective second fixing nuts with which the second hook and the fourth hook are respectively engaged to the second oblong hole and the second front end hole of the movable arm, are embedded into the movable arm, so as to align top surfaces of the respective second fixing nuts to a level not exceeding that of a top surface of the movable arm.

8. The rib spreader of claim 1, wherein:

the stationary arm has a detachable unit fixing a front end-side portion of the stationary arm in a detachable manner; and the movable arm has a detachable unit fixing a front end-side portion of the movable arm in a detachable manner.

* * * * *